United States Patent
Everaert et al.

(10) Patent No.: US 10,568,823 B2
(45) Date of Patent: Feb. 25, 2020

(54) METHOD OF STRENGTHENING HAIR FIBERS AND PROTECTING DYED HAIR COLOR FROM FADING OR WASH-OUT

(71) Applicant: HERCULES INCORPORATED, Wilmington, DE (US)

(72) Inventors: Emmanuel Paul Jos Marie Everaert, Rijsbergen (NL); Gijsbert Kroon, Hardinxveld-Giessendam (NL); Xiaochun Zhang, Barendrecht (NL)

(73) Assignee: HERCULES LLC, Wilmington, DE (US)

( * ) Notice: Subject to any disclaimer, the term of this patent is extended or adjusted under 35 U.S.C. 154(b) by 592 days.

(21) Appl. No.: 15/203,549

(22) Filed: Jul. 6, 2016

(65) Prior Publication Data

US 2017/0007518 A1    Jan. 12, 2017

Related U.S. Application Data

(60) Provisional application No. 62/190,922, filed on Jul. 10, 2015.

(51) Int. Cl.
| | |
|---|---|
| *A61Q 5/12* | (2006.01) |
| *A61K 8/42* | (2006.01) |
| *A61K 8/49* | (2006.01) |
| *A61Q 5/00* | (2006.01) |

(52) U.S. Cl.
CPC ............ *A61K 8/42* (2013.01); *A61K 8/498* (2013.01); *A61Q 5/004* (2013.01); *A61Q 5/12* (2013.01)

(58) Field of Classification Search
None
See application file for complete search history.

(56) References Cited

U.S. PATENT DOCUMENTS

| | | |
|---|---|---|
| 3,766,267 A | 10/1973 | Zak |
| 6,432,688 B1 | 8/2002 | Ito et al. |
| 9,028,804 B2 | 5/2015 | Nguyen et al. |
| 2009/0169502 A1 | 7/2009 | Quadir |
| 2013/0272980 A1 | 10/2013 | Nguyen et al. |
| 2013/0272981 A1 | 10/2013 | Nguyen et al. |

FOREIGN PATENT DOCUMENTS

| | | |
|---|---|---|
| CA | 2723348 A1 | 6/2011 |

*Primary Examiner* — Jyothsna A Venkat
(74) *Attorney, Agent, or Firm* — William J. Davis; Nathalie Tietcheu

(57) ABSTRACT

Disclosed is a method of strengthening hair fibers using a hair composition comprising an amide and/or an alkyl ammonium carboxylate salt. The amide can be a monoamide and/or a bisamide. A method of protecting dyed hair color from fading or wash-out using the hair composition is also included.

9 Claims, No Drawings

__US 10,568,823 B2__

METHOD OF STRENGTHENING HAIR FIBERS AND PROTECTING DYED HAIR COLOR FROM FADING OR WASH-OUT

CROSS REFERENCE TO RELATED APPLICATIONS

The present application claims the benefit under 35 U.S.C. 119 (e) of U.S. Provisional Patent Application Ser. No. 62/190,922, filed on Jul. 10, 2015, the entire content of which is hereby expressly incorporated herein by reference.

BACKGROUND OF THE INVENTION

1. Field of the Disclosed and Claimed Inventive Concepts

The presently disclosed and/or claimed inventive process(es), procedure(s), method(s), product(s), result(s), and/or concept(s) (collectively hereinafter referred to as the "presently disclosed and/or claimed inventive concept(s)") relates generally to a method of strengthening hair fibers using a hair composition comprising an amide and/or an alkyl ammonium carboxylate salt. A method of protecting dyed hair color from fading or wash-out using the hair composition is also included.

2. Background and Applicable Aspects of the Presently Disclosed and Claimed Inventive Concept(s)

Hair can suffer damage from a number of sources. The hair fiber can be damaged by environmental influences such as exposure to UV and chlorine; chemical influences such as dyeing, bleaching, perming, and over-frequent washing with harsh surfactant based cleansing shampoo compositions; and mechanical influences such as prolonged use of heated styling appliances. Consequently, the hair dries and becomes brittle, split ends are formed or the hair may break and lose its strength, while hair constituent proteins are eluted by treatments with shampoos, perm chemicals, hair dyes or the like and thus the proteins gradually disappear. Thus, with the elution of the proteins, the hair becomes thinner and the likelihood of damage increases. The hair, once damaged, is unable to restore itself to its original state. Therefore, it is necessary to protect the hair from damage, and in case of damage, to repair the damaged hair, in order to keep the hair beautiful and healthy.

It is well-known that the hair protein contains a lot of different chemical groups such as anionic, cationic groups consisting of sulfate, amino groups, hydrogen-bonding groups and etc. These groups provide many opportunities to repair, to strengthen and to improve/beautify the (damaged) hair. Based on these principles, many hair care products have been developed.

The coloring of hair has become increasingly popular in recent years. However, fading of artificial hair color has become a common problem and a frequent complaint by consumers. Fading can occur during the shampoo washing treatment as color wash-out, or can be initiated by environmental circumstances, such as by exposure to UV radiation. The washing process is the most significant factor in the removal of hair color, while UV exposure has a significant impact only after 90 hours of intense irradiation. Furthermore, the surfactants present in shampoo formulations provide a wetting function which brings moisture into the hair shaft, thus facilitating the removal of the dye molecules to exit during the water rinsing process. Maintaining hair color and minimizing hair color fading is highly desirable in the hair care market.

There still remains a need for topical hair treatment compositions which can strengthen hair, repair damaged hair and protect the dyed hair color.

Surprisingly, it has been found that a hair composition comprising an amide and/or an alkyl ammonium carboxylate salt can be used to strengthen the hair and repair the damaged hair. The hair composition can also be used to protect dyed hair color from fading or wash-out.

DETAILED DESCRIPTION OF THE INVENTIVE CONCEPT(S)

Before explaining at least one embodiment of the presently disclosed and/or claimed inventive concept(s) in detail, it is to be understood that the presently disclosed and/or claimed inventive concept(s) is not limited in its application to the details of construction and the arrangement of the components or steps or methodologies set forth in the following description or illustrated in the drawings. The presently disclosed and/or claimed inventive concept(s) is capable of other embodiments or of being practiced or carried out in various ways. Also, it is to be understood that the phraseology and terminology employed herein is for the purpose of description and should not be regarded as limiting.

Unless otherwise defined herein, technical terms used in connection with the presently disclosed and/or claimed inventive concept(s) shall have the meanings that are commonly understood by those of ordinary skill in the art. Further, unless otherwise required by context, singular terms shall include pluralities and plural terms shall include the singular.

All patents, published patent applications, and non-patent publications mentioned in the specification are indicative of the level of skill of those skilled in the art to which the presently disclosed and/or claimed inventive concept(s) pertains. All patents, published patent applications, and non-patent publications referenced in any portion of this application are herein expressly incorporated by reference in their entirety to the same extent as if each individual patent or publication was specifically and individually indicated to be incorporated by reference.

All of the compositions and/or methods disclosed herein can be made and executed without undue experimentation in light of the present disclosure. While the compositions and methods of the presently disclosed and/or claimed inventive concept(s) have been described in terms of preferred embodiments, it will be apparent to those of ordinary skill in the art that variations may be applied to the compositions and/or methods and in the steps or in the sequence of steps of the method described herein without departing from the concept, spirit and scope of the presently disclosed and/or claimed inventive concept(s). All such similar substitutes and modifications apparent to those skilled in the art are deemed to be within the spirit, scope and concept of the presently disclosed and/or claimed inventive concept(s).

As utilized in accordance with the present disclosure, the following terms, unless otherwise indicated, shall be understood to have the following meanings.

The use of the word "a" or "an" when used in conjunction with the term "comprising" may mean "one," but it is also consistent with the meaning of "one or more," "at least one," and "one or more than one." The use of the term "or" is used to mean "and/or" unless explicitly indicated to refer to alternatives only if the alternatives are mutually exclusive, although the disclosure supports a definition that refers to only alternatives and "and/or." Throughout this application, the term "about" is used to indicate that a value includes the inherent variation of error for the quantifying device, the method being employed to determine the value, or the variation that exists among the study subjects. For example, but not by way of limitation, when the term "about" is utilized, the designated value may vary by plus or minus twelve percent, or eleven percent, or ten percent, or nine percent, or eight percent, or seven percent, or six percent, or five percent, or four percent, or three percent, or two percent, or one percent. The use of the term "at least one" will be understood to include one as well as any quantity more than one, including but not limited to, 1, 2, 3, 4, 5, 10, 15, 20, 30, 40, 50, 100, etc. The term "at least one" may extend up to 100 or 1000 or more depending on the term to which it is attached. In addition, the quantities of 100/1000 are not to be considered limiting as lower or higher limits may also produce satisfactory results. In addition, the use of the term "at least one of X, Y, and Z" will be understood to include λ alone, Y alone, and Z alone, as well as any combination of X, Y, and Z. The use of ordinal number terminology (i.e., "first", "second", "third", "fourth", etc.) is solely for the purpose of differentiating between two or more items and, unless otherwise stated, is not meant to imply any sequence or order or importance to one item over another or any order of addition.

As used herein, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. The term "or combinations thereof" as used herein refers to all permutations and combinations of the listed items preceding the term. For example, "A, B, C, or combinations thereof" is intended to include at least one of: A, B, C, AB, AC, BC, or ABC and, if order is important in a particular context, also BA, CA, CB, CBA, BCA, ACB, BAC, or CAB. Continuing with this example, expressly included are combinations that contain repeats of one or more item or term, such as BB, AAA, MB, BBC, AAAB-CCCC, CBBAAA, CABABB, and so forth. The skilled artisan will understand that typically there is no limit on the number of items or terms in any combination, unless otherwise apparent from the context.

As used herein the term "hair" or "hair fiber(s)" be treated may be "living" i.e. on a living body or may be "non-living" i.e. in a wig, hairpiece or other aggregation of nonliving keratinous fibers. Mammalian, human hair is preferred. However wool, fur and other keratin containing fibers are suitable substrates for the compositions according to the presently disclosed and/or claimed inventive concept(s). "Hair" and "hair fiber(s) are used interchangeably in the presently disclosed and/or claimed inventive concept(s).

"Virgin hair" means hair that has never been treated chemically and/or mechanically including but not limited to coloring, bleaching, relaxing, straightening, perming, grooming, and exposures to sun, UV light, salty water, heat appliance, etc.

As used herein, the expression "leave-on compositions" designates compositions which are not rinsed with water once applied to the hair.

As used herein, the expression"rinse-off compositions" designates compositions which are rinsed with water once applied to the hair.

As used herein, the expression "dyed hair" means hair which has been colored with a permanent, semi-permanent or temporary artificial color, which can be different from the original color of the hair.

As used herein, the expression "dyed hair color fading" means the color erosion of dyed hair.

The presently disclosed and/or claimed inventive concept(s) relates generally to a method of strengthening hair fibers comprising applying a hair composition comprising an amide and/or an alkyl ammonium carboxylate salt. The amide can be a monoamide and/or a bisamide. The hair fibers can include virgin hair and damaged or weakened hair fibers.

In one non-limiting embodiment, the hair composition can be represented by Formula (I), or Formula (II), or Formula (I) and Formula (II).

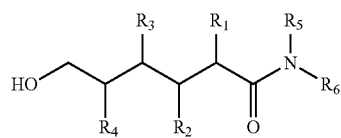

Formula (I)

wherein $R_1$-$R_4$ are independently hydrogen, a hydrocarbon radical having 1 to about 10 carbon atoms, a hydroxyl group, an amino group, a sulfhydryl group, an aryl group, or a halogen; and $R_5$ and $R_6$ are independently hydrogen, an aliphatic hydrocarbon group, an alicyclic hydrocarbon group, an aryl group, an alkylaryl group, or a heterocyclic group. The aliphatic hydrocarbon group, the alicyclic hydrocarbon group, the aryl group, the alkylaryl group, or the heterocyclic group can be substituted with at least one hydroxyl group.

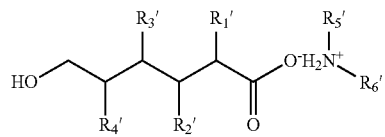

Formula (II)

wherein $R'_1$-$R'_4$ are independently hydrogen, a hydrocarbon radical having 1 to about 10 carbon atoms, a hydroxyl group, an amino group, a sulfhydryl group, an aryl group, an alkylaryl group or a halogen; and $R'_5$ and $R'_6$ are independently hydrogen, an aliphatic hydrocarbon group, an alicyclic hydrocarbon group, an aryl group, an alkylaryl group, or a heterocyclic group, excluding $R'_5$ and $R'_6$ being simultaneous hydrogens. The aliphatic hydrocarbon group, the alicyclic hydrocarbon group, the aryl group, the alkylaryl group or the heterocyclic group can be substituted with at least one hydroxyl group.

The amounts of Formula (I) and Formula (II) can be varied when the hair composition comprises Formulas (I) and (II). The mole percentages of Formula (I) to Formula (II) can be varied from 0.1 mole % to 99.9 mole %. In one non-limiting embodiment, the molar ratio of Formula (I) to Formula (II) can be 1:99 to 99:1. In another non-limiting embodiment, the molar ratio of Formula (I) to Formula (II) can be 20:80 to 80:20. In yet another non-limiting embodiment, the molar ratio of Formula (I) to Formula (II) can be 40:60 to 60:40.

In another non-limiting embodiment, the hair composition can be represented by formulations selected from the group consisting of Formula (III), Formula (IV), Formula (V), and combinations thereof.

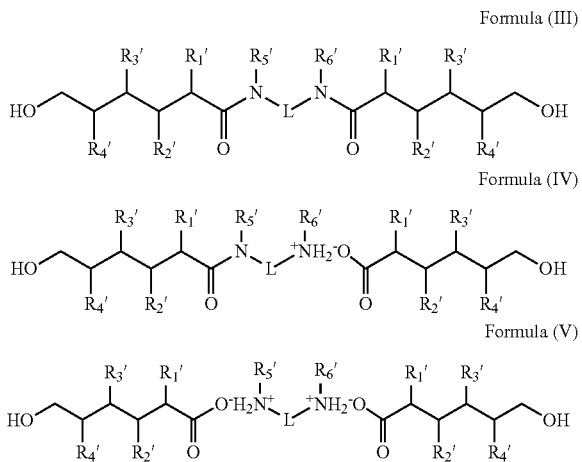

Formula (III)

Formula (IV)

Formula (V)

wherein $R'_1$-$R'_4$ are independently hydrogen, a hydrocarbon radical having 1 to about 10 carbon atoms, a hydroxyl group, an amino group, a sulfhydryl group, an aryl group, or a halogen; and $R'_5$ and $R'_6$ are independently hydrogen, an aliphatic hydrocarbon group, an alicyclic hydrocarbon group, an aryl group, an alkylaryl group, or a heterocyclic group. L is a linker and can be an aliphatic hydrocarbon group, an alicyclic hydrocarbon group, an aryl group, an alkylaryl group, or a heterocyclic group. The aliphatic hydrocarbon group, the alicyclic hydrocarbon group, the aryl group, the alkylaryl group or the heterocyclic group can be further substituted by other functional groups containing oxygen, sulfur, nitrogen, halogen, and etc.

The molar ratios of Formula (III)+Formula (IV) to Formula (V) can be varied when the hair composition comprises Formulas (III), (IV) and (V). In one non-limiting embodiment, the molar ratio of Formula (III)+Formula (IV) to Formula (V) can be 1:99 to 99:1. In another non-limiting embodiment, the molar ratio of Formula (III)+Formula (IV) to Formula (V) can be 20:80 to 80:20. In yet another non-limiting embodiment, the molar ratio of Formula (III)+Formula (IV) to Formula (V) can be 40:60 to 60:40.

The hair composition of Formula (I), and/or Formulation (II) can comprise a reaction product of at least one lactone compound and at least one amino alcohol compound. The amino alcohol compound can comprise one, two, three, or more hydroxyl groups.

In one non-limiting embodiment, the amino alcohol compound can be represented by Formula (VI):

Formula (VI)

wherein $R_1$ and $R_2$ each represents an aliphatic hydrocarbon group, an alicyclic hydrocarbon group, an aryl group, or a heterocyclic group, where these groups are substituted with at least one hydroxyl group; and $R_3$ is hydrogen or an alkyl group having 1 to about 12 carbon atoms.

The aliphatic hydrocarbon group used herein can include saturated or unsaturated, liner or branched, substituted or unsubstituted aliphatic hydrocarbon groups. Examples of the aliphatic hydrocarbon groups can include, but are not limited to, a straight or branched alkyl group having 1 to about 12 carbon atoms, such as a methyl group, an ethyl group, a propyl group, an isopropyl group, a butyl group, an isobutyl group, an sec-butyl group, a t-butyl group, a pentyl group, a hexyl group, an octyl group, and a decyl group; an alkenyl group having 1 to 12 carbon atoms, such as a vinyl group, an allyl group, a 1-propenyl group, an isopropenyl group, and a 2-butenyl group; and an alkynyl group having 1 to 12 carbon atoms, such as a 2-propynyl group, and a 2-butynyl group.

The alicyclic hydrocarbon group used herein can include saturated or unsaturated, substituted or unsubstituted alicyclic hydrocarbon groups, Examples of the alicyclic groups can include, but are not limited to, a cycloalkyl group having about 3 to about 10 carbon atoms, such as a cyclobutyl group, a cyclopentyl group, a cyclohexyl group, a cyclooctyl group; and a cycloalkenyl group having about 3 to about 10 carbon atoms, such as a cyclopentenyl group, and a cyclohexenyl group.

The aryl group used herein can comprise about 6 to about 14 carbon atoms, such as a phenyl group, and a naphthyl group.

The heterocyclic group used herein can include those containing at least one heteroatom selected from the group consisting of a nitrogen atom, an oxygen atom, and a sulfur atom. The heterocyclic group may be an aromatic heterocyclic group, a non-aromatic heterocyclic group, or a compound heterocyclic group.

A heterocyclic ring of the above-mentioned heterocyclic group can include a nitrogen-containing heterocyclic ring such as pyrroline, pyrrole, piperidine, piperazine, pyridine, pyrimidine, pyridazine, triazole, and quinoline; an oxygen-containing heterocyclic ring such as tetrahydrofuran, furan, and pyran; a sulfur-containing heterocyclic ring such as tetrahydrothiophene, and thiophene; and a heterocyclic ring containing at least two heteroatoms selected from the group consisting of a nitrogen atom, an oxygen atom, and a sulfur atom, such as thiazoline, thiazolidine, thiazole, thiazine, and morpholine.

In another non-limiting embodiment, the amino alcohol compound can be represented by Formula (VII):

Formula (VII)

where $R_1$ and $R_2$ are independently H, an alkyl group having 1 to about 20 carbon atoms, or an alkyl group having 1 to about 20 carbon atoms substituted with at least one hydroxyl group; and R is an alkyl or alkenyl having about 2 to about 16 carbon atoms.

In yet another non-limiting embodiment, the amino alcohol compound can be represented by Formula (VIII):

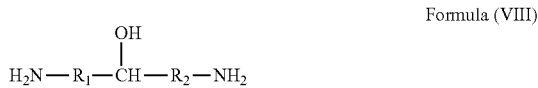

Formula (VIII)

where $R_1$ and $R_2$ are an alkyl group having 1 to about 20 carbon atoms, or an alkyl group having 1 to about 20 carbon atoms substituted with at least one hydroxyl group.

Examples of the amino alcohol compound can include, but are not limited to, ethanolamine, 2-hydroxyethylhydrazine, 2-methoxyethylamine, 3-amino-1-propanol, amino-2-propanol, 3-amino-1,2-propaediol, serinol, 1,3-diamino-2-propanol, 1-amino-2-methyl-2-propanol, 2-(ethylamino)ethanol, 2-amino-1-butanol, 2-amino-2-methyl-1propanol, 3-methylamino-1-propanol, 4-amino-1-butanol, 2-(2-aminoethoxy)ethanol, 3-methylamino-1,2-propanediol, diethanolamine, tris(hydroxymethyl)aminomethane, N-(2-hydroxyethyl)ethylenediamine, meso-1,4-diamino-2,3-butanediol, 2-aminocyclopentanol, 2-(isopropylamino)ethanol, 2-(propylamino)ethanol, 2-amino-3-methyl-1-butanol, 5-amino-1-pentanol, 2-(3-aminopropylamino)ethanol, 1-amino-1-cyclopentanemethanol, 4-aminocyclohexanol, 2-(butylamino)ethanol, 6-amino-1-hexanol, DL-2-amino-1-hexanol, leucinol, N,N'-bis(2-hydroxyethyl)ethylenediamine, 2-aminobenzyl alcohol, 3-aminolbenzyl alcohol, 4-aminobenzyl alcohol, 2-amino-4-methoxyphenol, 3,4-dihydroxybenzylamine, dihydroxybenzylamine, 1-aminomethyl-1-cyclohexanol, 2-aminomethyl-1-cyclohexanol, N-Boc-ethanolamine, 5-amino-2,2-dimethylpentanol, 2-amino-1-phenylethanol, 2-amino-3-methylbenzyl alcohol, 2-amino-5-methylbenzyl alcohol, 2-aminophenylethyl alcohol 3-amino-2-methylbenzyl alcohol, 3-amino-4-methylbenzyl alcohol, 4-(1-hydroxyethyl)aniline, 4-aminophenethyl alcohol, N-(2-hydroxyethyl)aniline, 3-hydroxy-4-methoxybenzylamine, 3-hydroxytyramine, 6-hydroxydopamine, 4-(Z-amino)-1-butanol, 5-(Z-amino)-1-pentanol, 4-(Z-amino)cyclohexanol, 6-(Z-amino)-1-hexanol, 3-(Boc-amino)-1-propanol, N-Boc-serinol, 2-benzylaminoethanol, 4-(Boc-amino)-1-butanol, 2-(aminomethyl)-2-(hydroxymethyl)-1,3-propanediol, and 2-(2-aminoethyl)-2-(hydroxymethyl)-1,3-propanediol.

The hair composition of Formula (III), or Formula (IV) or Formula (V) or the combinations can comprise a reaction product of at least one lactone compound and at least one alkyl diamine compound.

The alkyl diamine compound can contain about 2 to about 12 carbon atoms. In one non-limiting embodiment, the alkyl diamine compound can contain about 2 to about 6 carbon atoms. Examples of the alkyl diamine compound can include, but are not limited to, ethylenediamine, 1,3-diaminopropane, 1,4-diaminobutane, 1,5-diaminopentane, hexamethylene diamine, 1,7-diaminohepatane, 1,8-diaminooctane, 1,9-nonanediamine, 1,10-diaminodecane, and dodecanethylenediamine. In one non-limiting embodiment, the alkyl diamine is ethylenediamine. In another non-limiting embodiment, the alkyl diamine is 1,3-diaminopropane.

The lactone compound of the presently disclosed and/or claimed inventive concept(s) can include, but are not limited to, a cyclic ester compound comprising a heterocyclic ring and the heteroatom on the heterocyclic ring is oxygen, which can be represented by Formula (IX):

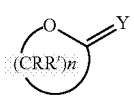

Formula (IX)

wherein R and R' are independently H and a hydrocarbon radical containing from 1 to about 40 carbon atoms that may be saturated or unsaturated, linear or branched, substituted or unsubstituted. The hydrocarbon radicals can comprise hydroxyl groups, amino groups, sulfhydryl groups, aryl groups and halogens. n is an integer of 1 to about 10. Y is oxygen or sulfur. The heterocyclic ring can be saturated or unsaturated.

The lactone compound can comprise 3- to 8-membered rings (including the oxygen on the heterocyclic ring and the carbonyl carbon). Examples of such lactone compounds can include, but are not limited to, α-lactones (3-membered ring alpha-lactones), β-lactones (4-membered ring beta-lactones), γ-lactones (5-membered ring gamma-lactones), δ-lactones (6-membered ring delta-lactones) and ε-lactones (8-membered ring epsilon-lactones).

In one non-limiting embodiment, the lactone compound can be a δ-lactone. In one non-limiting embodiment, the δ-lactone can be represented by Formula (X):

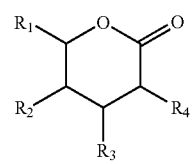

Formula (X)

wherein $R_1$-$R_4$ are independently H, a hydrocarbon radical having 1 to about 10 carbon atoms, a hydroxyl group, an amino group, a sulfhydryl group, an aryl group, or a halogen.

In one non-limiting embodiment, $R_1$-$R_4$ are independently a hydrocarbon radical being linear or branched, saturated or unsaturated, or substituted or unsubstituted.

Examples of the δ-lactone compounds can include, but are not limited to, meadowfoam δ-lactone, δ-octalactone, δ-decalactone, δ-nonalactone, undecanoic δ-lactone, δ-dodecalactone, massoia lactone (or 5-pentylpent-2-en-5-olide), jasmine lactone (or Z-2-pentenylpentan-5-olide), 6-pentyl-alpha-pyrone (or 5-pentylpenta-2,4-dien-5-olide) δ-valerolactone, galactonolactone, glucono δ-lactone, hexadecanolactone, and mevalonolactone.

According to the presently disclosed and/or claimed inventive concept(s), the lactone compound, the alkyl diamine compound or amino alcohol compound, and a solvent can be mixed together at room temperature (~23° C.) to form a mixture. The mixture can be heated to about 30° C. to about 100° C. for at least 30 minutes to form a reaction product of the presently disclosed and/or claimed inventive concept(s). In one non-limiting embodiment, the mixture can be heated to about 40° C. to about 80° C. for at least 60 minutes. In another non-limiting embodiment, the mixture can be heated to about 50° C. to about 75° C. for at least 120 minutes. In yet another non-limiting embodiment, the mixture can be heated to about 55° C. to about 65° C. for at least 150 minutes.

The solvent can be water; methanol; acetone; benzene; the other alcohols and/or glycols including but not limited to ethanol, isopropanol (IPA), tert-butyl alcohol (TBA), glycol, ethylene glycol, propylene glycol, diethylene glycol, and dipropylene glycol; and mixtures thereof. In one non-limiting embodiment, the solvent is water. In another non-limiting embodiment, the solvent is methanol. In yet another embodiment, the solvent is a mixture of water with methanol, ethanol, or isopropanol.

The appropriate amounts of the lactone compound and the alkyl diamine or amino alcohol compound can be determined by a skilled artisan. In one non-limiting embodiment, the molar ratio of the lactone compound to the alkyl diamine compound or amino alcohol compound ranges from about 10:1 to about 1:10. In another non-limiting embodiment, the molar ratio of the lactone compound to the alkyl diamine compound or amino alcohol compound ranges from about 8:1 to about 1:8. In yet another non-limiting embodiment, the molar ratio of the lactone compound to the alkyl diamine compound or amino alcohol compound ranges from about 5:1 to about 1:5. In yet another non-limiting embodiment, the molar ratio of the lactone compound to the alkyl diamine compound or amino alcohol compound ranges from about 2:1 to about 1:2.

In order to obtain the maximum hair strength, the hair care composition hereinafter further comprises a sufficient quantity of a buffer system to adjust a pH to about 2 to about 6. The buffer system can be any combination of an acid and a base. Typically, the buffer system comprises an inorganic and/or an organic acid and/or a salt thereof to provide the hair care composition with a pH value from about 2 to about 6 at 25° C. In one non-limiting embodiment, the pH value can range from about 3 to about 5. In another non-limiting embodiment, the pH value can range from about 3 to about 4.

In one aspect of the buffering system, the inorganic acid is selected from the group consisting of hydrogen chloride (HCl), sulfuric acid ($H_2SO_4$), nitric acid ($HNO_3$), phosphoric acid ($H_3PO_4$), and combinations thereof.

In another aspect of the buffering system, the organic is selected from the group consisting of an alpha-hydroxy acid, a polycarboxylic acid, and combinations thereof. Accordingly, the organic acid has an acidic functional group having a pKa of about 4.5 or less. In one non-limiting embodiment, the organic has a second acidic functional group having a pKa of about 6 or less.

The organic acid may have a molecular weight less than about 500 grams per mole (g/mol). For example, but not by way of limitation, the molecular weight of the organic acid may be from about 90 g/mol to about 400 g/mol, or from about 100 g/mol to about 300 g/mol, or from about 130 g/mol to about 250 g/mol, or from about 150 g/mol to about 200, or about 190 g/mole. In another aspect, the organic acid may be soluble in water in an amount greater than about 0.2 moles per liter at 25° C. For example, but not by way of limitation, the water solubility of the organic acid may be about 0.3 mol/L or more, or about 0.4 mol/L or more, or about 0.5 mol/L or more.

Examples of the organic acids can include, but are not limited to, lactic acid, citric acid, tartaric acid, gluconolactive acid, pimelic acid, glyoxylic acid, aconitic acid, ethylenediaminetetraacetic acid, L-glutamic acid, malic acid, malonic acid, and combinations thereof.

Examples of the salt of such an inorganic acid and an organic acid can include its alkali metal salts such as the sodium salt and the potassium salt; its ammonium salt; and s alkanolamine salts such as the triethanolamine salt.

The hair composition of the presently disclosed and/or claimed inventive concept(s) can further comprise at least one active hair benefit component. The active hair benefit component can include, but are not limited to, a rheology modifier, a surfactant, an auxiliary fixative, a solvent, water, a conditioner, a propellant, a neutralizing agent, fragrance, a fragrance solubilizer, a thickener, preservative, an emulsifier, emollient, humectant, colorant, wax, and mixtures thereof.

Other active hair benefit components can include, but are not limited to, fatty acid soap, suspending aids, vitamins, hair growth promoters, self-tanning agents, sunscreens, antidandruff agents, anti-inflammatory compounds, analgesics, antiperspirant agents, deodorant agents, hair fixatives, particulates, abrasives, moisturizers, antioxidants, keratolytic agents, anti-static agents, foam boosters, hydrotropes, solublizing agents, chelating agents, antimicrobial agents, antifungal agents, pH adjusting agents, chelating agents, buffering agents, botanicals, oxidizing agents, reducing agents, hair bleaching agents, pigments, anticaries, anti-tartar agents, and anti-plaque agents.

The surfactant can be an anionic surfactant, a cationic surfactant, an amphoteric and zwitterionic surfactant, a nonionic surfactant and combinations thereof.

Examples of the anionic surfactants can include, but are not limited to, the alkyl sulphates, alkyl ether sulphates, alkaryl sulphonates, alkanoyl isethionates, alkyl succinates, alkyl sulphosuccinates, N-alkyl sarcosinates, alkyl phosphates, alkyl ether phosphates, alkyl ether carboxylates, and alpha-olefin sulphonates, especially their sodium, magnesium, ammonium and mono-, di- and triethanolamine salts. The alkyl and acyl groups generally contain from 8 to 18 carbon atoms and may be unsaturated. The alkyl ether sulphates, alkyl ether phosphates and alkyl ether carboxylates may contain from 1 to 10 ethylene oxide or propylene oxide units per molecule.

Typical anionic surfactants for use in the hair composition of the presently disclosed and/or claimed inventive concept(s) can include, but are not limited to, sodium oleyl succinate, ammonium lauryl sulphosuccinate, ammonium lauryl sulphate, sodium dodecylbenzene sulphonate, triethanolamine dodecylbenzene sulphonate, sodium cocoyl isethionate, sodium lauryl isethionate and sodium N-lauryl sarcosinate. In one non-limiting embodiment, anionic surfactants can be sodium lauryl sulphate, triethanolamine monolauryl phosphate, sodium lauryl ether sulphate 1 EO, 2EO and 3EO, ammonium lauryl sulphate and ammonium lauryl ether sulphate 1EO, 2EO and 3EO.

Examples of amphoteric and zwitterionic surfactants can include, but are not limited to, alkyl amine oxides, alkyl betaines, alkyl amidopropyl betaines, alkyl sulphobetaines (sultaines), alkyl glycinates, alkyl carboxyglycinates, alkyl amphopropionates, alkylamphoglycinates, alkyl amidopropyl hydroxysultaines, acyl taurates and acyl glutamates, wherein the alkyl and acyl groups have from 8 to 19 carbon atoms. Typical amphoteric and zwitterionic surfactants for use in the hair composition of the presently disclosed and/or claimed inventive concept(s) can include lauryl amine oxide, cocodimethyl sulphopropyl betaine and preferably lauryl betaine, cocamidopropyl betaine and sodium cocamphopropionate.

The hair composition can also include co-surfactants, to help impart aesthetic, physical or cleansing properties to the composition. In one non-limiting embodiment, the nonionic surfactant can be included in an amount ranging from 0% to about 5% by weight based on total weight of the hair composition.

For example, representative nonionic surfactants in the hair compositions of the presently disclosed and/or claimed inventive concept(s) can include condensation products of aliphatic ($C_8$-$C_{18}$) primary or secondary linear or branched chain alcohols or phenols with alkylene oxides, usually ethylene oxide and generally having from 6 to 30 ethylene oxide groups.

Other representative nonionics include mono- or di-alkyl alkanolamides, Examples include coco mono- or di-ethanolamide and coco mono-isopropanolamide.

Further nonionic surfactants which can be included in the hair compositions of the presently disclosed and claimed inventive concept(s) are the alkyl polyglycosides (APGs).

Typically, the APG is one which comprises an alkyl group connected (optionally via a bridging group) to a block of one or more glycosyl groups. Preferred APGs are defined by the following formula:

RO-(G)$_n$ wherein R is a branched or straight chain alkyl group which may be saturated or unsaturated and G is a saccharide group.

R may represent a mean alkyl chain length of from about C$_5$ to about C$_{20}$. Preferably R represents a mean alkyl chain length of from about C$_8$ to about C$_{12}$. Most preferably the value of R lies between about 9.5 and about 10.5. G may be selected from C$_5$ or C$_6$ monosaccharide residues, and is preferably a glucoside. G may be selected from the group comprising glucose, xylose, lactose, fructose, mannose and derivatives thereof. Preferably G is glucose.

The degree of polymerization, n, may have a value of from 1 to about 10 or more. Preferably, the value of n lies in the range of from about 1.1 to about 2. Most preferably the value of n lies in the range of from about 1.3 to about 1.5.

Suitable alkyl polyglycosides for use in the presently disclosed and/or claimed inventive concept(s) are commercially available and include for example those materials identified as: Oramix™ NS10 (available from Seppic); Plantaren™ 1200 and Plantaren™ 2000 (available from Henkel).

The conditioning agent can be silicones, organic conditioning oils, natural and synthetic waxes, and cationic polymers.

The silicone can be silicone fluids, silicone oils, cationic silicones, silicone gums, high refractive silicones, silicone resins, emulsified silicones, and dimethicone copolyols.

The rheology modifier or the rheology modifying polymer comprises a polymer selected from the group consisting of carboxymethyl cellulose, hydroxyethyl cellulose, hydroxypropyl cellulose, hydroxypropylmethyl cellulose, hydroxypropyl guar, hydroxymethyl hydroxyethyl cellulose, and combinations thereof.

The hair composition in the presently disclosed and/or claimed inventive concept(s) can also be used to protect hair color against fading and/or shampoo washings. The color protection treatment can be delivered by a post-color treatment (after dyeing of hair), either from a leave-in product or a rinse-off production or a combination thereof.

The following examples illustrate the presently disclosed and/or claimed inventive concept(s), parts and percentages being by weight, unless otherwise indicated. Each example is provided by way of explanation of the presently disclosed and claimed inventive concept(s), not limitation of the presently disclosed and claimed inventive concept(s). In fact, it will be apparent to those skilled in the art that various modifications and variations can be made in the presently disclosed and claimed inventive concept(s) without departing from the scope or spirit of the invention. For instance, features illustrated or described as part of one embodiment, can be used on another embodiment to yield a still further embodiment. Thus, it is intended that the presently disclosed and claimed inventive concept(s) covers such modifications and variations as come within the scope of the appended claims and their equivalents.

EXAMPLES

Preparation of Reaction Products

Example 1—Reaction of Gluconolactone with Ethylene Diamine in Water 3.2 g ethylene diamine (EDA), 23.9 g water and 35.6 g L-gluconic acid delta-lactone (GDL) were sequentially added into a 3-neck flask to form a mixture. Under nitrogen, the mixture was gradually heated to about 60° C. and kept for about 2.5 hours. Then, the temperature was decreased to 50° C. and the formed end product was poured into a container. Once the temperature was lowered to room temperature (~21-23° C.), the end product was obtained. Analytical results showed that the end product included N,N'-ethylenebis-D-gluconamide, N-(2-aminoethyl)-D-gluconamide, and GDL.

Example 2—Reaction of GDL with Ethanolamine in Water 6.16 g ethanolamine (EA), 15 g water and 17.9 g L-gluconic acid delta-lactone were sequentially added into a 3-neck flask to form a mixture. Under nitrogen, the mixture was gradually heated to about 60° C. and kept at that temperature for about 2.5 hours. Then, the temperature was decreased to 50° C. and the formed end product was poured into a container. Once the temperature was lowered to room temperature (~21-23° C.), the end product was obtained.

Example 3—Reaction of FDL with Ethylene Diamine in Methanol 2.40 g ethylenediamine, 79 g methanol and 14.26 g L-gluconic acid delta-lactone were sequentially added into a 3-neck flask to form a mixture. Under nitrogen, the mixture was gradually heated to reflux and kept at that temperature for about 2.5 hours. Then, the temperature was decreased to room temperature (~21-23° C.). The final product was filtered and dried. The white powder product was obtained.

Example 4—Reaction of GDL with 3-Amino-1-Propanol in Water 15.0 g 3-amino-1-propanol (APA), 35.6 g L-gluconic acid delta-lactone and 50 g water were sequentially added into a 3-neck flask to form a mixture. Under nitrogen, the mixture was gradually heated to about 75° C. and kept at that temperature for about 2.5 hours. Then, the temperature was decreased to 50° C. and the formed end product was poured into a container. Once the temperature was lowered to room temperature (~21-23° C.), the end product was obtained.

Example 5—Reaction of GDL with 3-Amino-1-Propanol in Methanol 5.0 g (0.2 moles) 3-amino-1-propanol, 200 g methanol and 35.6 g (0.2 moles) L-gluconic acid delta-lactone (GDL) were sequentially added into a 3-neck flask. The mixture was gradually heated under nitrogen to reflux at 60° C. and kept at that temperature for about 2.5 hours. The reaction was allowed to cool to ambient temperature (~21-23° C.). The reaction mixture was filtered and the product was dried in a ventilated oven at 60° C. to give a gluconamide as a white powder.

Example 6—Reaction of GDL with Tris(Hydroxymethyl)Aminomethane in Methanol 54.0 g L-gluconic acid delta-lactone, 18.3 g ethanolamine and 300 g methanol were sequentially added into a 3-neck flask to form a mixture. Under nitrogen, the mixture was gradually heated to reflux and kept at that temperature for about 2.5 hours. Then, the temperature was decreased to room temperature (~21-23° C.). The final product was filtered and dried. The white powder product was obtained.

Example 7—Reaction of GDL with Tris(Hydroxymethyl)Aminomethane in Water 50.0 g L-gluconic acid delta-lactone, 34.0 g tris(hydroxymethyl)aminomethane (THMAM) and 70.2 g water were sequentially added into a 3-neck flask to form a mixture. Under nitrogen, the mixture was gradually heated to about 75° C. and kept at that temperature for about 2.0 hours. Then, the temperature was decreased to 50° C. and the formed end product was poured into a container. The end product containing 55 wt % of solids in water was obtained.

Example 8—Mixture of GDL with 3-Amino-1-Propanol in Water 5.8 g of gluconic acid (50 wt % in water) and 7.5 g of 3-amino-1-propanol were mixed in a beaker at room temperature (~21-23° C.) for 1 hour.

Measurement of the Reaction Products
Sample Preparation:
For aqueous samples: About 200 mg of the sample was dissolved in 1.3 g $D_2O$ to form a solution. The sample solution was then transferred to a 5 mm NMR tube for analysis.

For solid samples: About 100 mg of the sample was dissolved in 1.4 g $D_2O$ to form a solution. The sample solution was transferred to a 5 mm NMR tube for analysis.

NMR Measurement:
Quantitative $^1H$ NMR spectrum was recorded using a Varian 400 MHz NMR spectrometer using PFG-1 probe. Acquisition parameters were as follows:
Temperature 297K,
Sweep width 16 ppm,
Pulse width 90 deg.,
Number of scans 16, and
Relaxation delay 30 s.

The spectrum was phase and baseline corrected using standard practice. The spectrum was calibrated assigning the trimethylsilyl propanoic acid (TSP) reference peak to 0.0 ppm.

For the Reaction Products of Diamine (EDA) and GDL:
Region A ($I_A$)=3.50-3.40 ppm (singlet)
Region B ($I_B$)=3.4-3.25 ppm (singlet)
Region C (k)=3.25-3.10 ppm (triplet)
Diamide/Monoamide/Amine-Gluconic Acid Salt Molar Ratios were Calculated as Follows:

Diamide=$(I_A)/(I_A+I_B+2I_C)$.

Monoamide=$(2I_C)/(I_A+I_B+2I_C)$.

Amine-Gluconic Acid Salt=$(I_B)/(I_A+I_B+2I_C)$.

For the Reaction Product of Amine Alcohol Compound (EA/APA) and GDL:
Region A ($I_A$)=4.40-4.20 ppm (doublet)
Region B ($I_B$)=4.25-4.10 ppm (doublet)
Monoamide/Amine-Gluconic Acid Salt Molar Ratios were Calculated as Follows:

Monoamide=$(I_A)/(I_A+I_B)$.

Amine-Gluconic Acid Salt=$(I_B)/(I_A+I_B)$.

Table 1 lists the measurement results of the reaction products from Examples 1-7.

TABLE 1

| Sample | GDL/Amine (Molar Ratio) | Mole % Monoamide | Mole % Diamide | Mole % Amine-Gluconic Acid Salt |
|---|---|---|---|---|
| Example 1 | 2:1 | 42 | 56 | 2 |
| Example 2 | 1:1 | 54 | — | 46 |
| Example 3 | 1:1 | 88 | 10 | 2 |
| Example 4 | 1:1 | 59 | — | 41 |
| Example 5 | 1:1 | >99 | — | <1 |
| Example 6 | 1:1 | >99 | — | <1 |
| Example 7 | 1:1 | 7 | — | 93 |

Hair Strengthening Test
Virgin dark Caucasian hair was used (available from International Hair Importers, Glendale, N.Y., USA). Double-bleached dark Caucasian hair was obtained by bleaching the virgin dark Caucasian hair for 60 minutes with two parts of 12% $H_2O_2$ cream and one part of bleaching powder Lock-blond Blue (potassium persulfate, available from Hair Beauty & Care, Belgium). The double-bleached hair was then rinsed and washed with 4.5 wt % of basic SLES solution.

1. Measurement of Survival Characteristic Life Time

The end products obtained from Examples 1-5 and 7-8 were directly diluted with water into 1 wt % of aqueous solutions. The pH of the aqueous solutions was adjusted to about 4 using lactic acid or lactic acid/sodium hydroxide in Example 1 and tartaric acid or tartaric acid/sodium hydroxide in other Examples. A section of hair fibers (>50 hair fibers, hereinafter "the hair") was cut from the top of the hair switch. The hair was soaked into the aqueous solution for about 30 minutes without agitation. Then the hair was taken out and dried at a controlled temperature of 23±2° C. and a controlled room humidity of 50±5%. The middle part of each hair fiber was cramped with PVC-lined brass crimps. After each hair fiber was crimped, the hair was kept for at least 2 hours at the controlled temperature and the controlled room humidity for equilibrating.

A Cyclic Tester (CYC 801) was used for cyclic tensile test and measurement, along with an automatic hair sample loading module ASL1500 (loaded with 50 hair fibers) and a Fiber Dimensional Analysis System (FDAS 765 Model) which is incorporated with Mitituyo Laser Micrometer LSM 500 for measuring the diameter for each hair fiber. The instrument and its accessories were available from Dia-Stron Limited, Andover, UK.

The diameter of each hair fiber was measured and averaged over five measurements before the cyclic tensile test. Measurement of survival characteristics of the virgin and damaged or weaken hair with and without treatment using the reaction products of the presently disclosed and/or claimed inventive concept(s) was conducted under repeated tensile loading. The loading force was calculated based on the measured diameter of each hair fiber and applied to the corresponding fiber so that the constant stress (gram/hair cross section surface area) was applied to the single hair fiber. Fifty (50) hair fibers were loaded for repeating measurement with a speed of 40 mm per minute. The tensile test was ended when all of the hair fibers were broken or reached the maximum cycles of 100,000. The cycle number of breaking each hair fiber was recorded. The survival probabilities of the treated and untreated (control) hair fibers versus cycle numbers were obtained using UvWin OC Application Software (available from Dia-Stron Limited UK), which was based on Weibull analysis. The data are shown in Table 2 (using 0.0165 g/$\mu m^2$ stress control) and Table 3 (using 0.0140 g/μm² stress control). The Weibull α-parameter or characteristic life time was the cycle numbers for breaking 63.2% of the hair fibers. For each test group, the normalized data was calculated based on the following equation:

$$\text{Normalized Data} = \frac{\text{Chracteristic Life Time for Treated Hair}}{\text{Characteristic Life Time for Untreated Hair}} \times 100$$

2. Differential Scanning Calorimetry (DSC) Measurement

DSC is based on the fact that all materials have abilities to absorb certain amounts of energy on heating. This amount of energy is sensitive to changes in the structure, phase, and composition of the material. For example, the amount of energy that the material absorbs may change when the material undergoes a change in crystal structure, phase transition such as melting, or loss of water.

DSC techniques published earlier by Cao (J. Cao, Melting Study of the Crystallites in Human Hair by DSC, Thermody. Acta, 335 (1999) and F. J. Wortmann (F. J Wortmann, C. Springob, and G. Sendlebach, Investigations of Cosmetically Treated Human Hair by DSC in Water, IFFCC. Ref 12 (2000) are used to study the structural changes of hair by measuring the thermal decomposition pattern or behavior. The thermal stability of hair is evaluated by measuring the amount of thermal energy required for denaturation or phase transition. The technique measures the amount of heat transferred into and out of a sample in a comparison to a reference. The heat transfer in (endothermic) and out (exothermic) is detected and recorded as a thermogram of heat flow versus temperature.

The DSC technique yields thermogram data on the denaturation temperature $T_d$ and the denaturation enthalpy (delta H) of hair. It is concluded that the thermogram data of the denaturation temperature $T_d$ of hair is dependent on the crosslink density of the matrix in which surrounds the microfibrils or crystalline filaments. Also, the denaturation enthalpy (delta H) depends on the strength of the crystalline filaments or microfibrils. It has been shown that cosmetic treatments, such as bleaching or perming, affect these morphological components selectively and differently at different rates causing changes in denaturation temperatures and in heat flow. The lower the denaturation temperature the more damaged is the hair.

DSC was used to analyze the effects of the treatment in the presently disclosed and/or inventive concept(s). The hair samples were analyzed using TA Instrument DSC Q-2000. Linear baseline was used to determine denaturation enthalpy.

The end products obtained from Examples 1-5 and 7-8 were directly diluted to 1 wt % of aqueous solutions. The pH of the aqueous solutions was adjusted to about 4 using lactic acid or lactic acid/sodium hydroxide in Example 1 and tartaric acid or tartaric acid/sodium hydroxide in other Examples. The hair was soaked in the aqueous solution for about 30 minutes. Then the hair was rinsed with tap water for about 20 to about 30 seconds. The hair was dried by patting with paper towels to remove excess water. While damp, the hair was cut into 2-4 mm in length with scissors and then was dried at ambient temperature conditions and relative humidity (20-23 C.°, 50-55% RH) for about five minutes. The hair was weighed to about 5 to 7.5 mg and put into a high pressure stainless steel pan. About 45 ml of water was added into the pan. Five pans were prepared for each hair fiber. The hair fibers were equilibrated at 20° C. for about two minutes. The hair fibers were heated up to 175° C. at 2° C. per minute. The hair fibers were then cooled down to 20° C. at 20° C. per minute. The hair fibers were equilibrated at 25° C. The measured data was listed in Tables 2 and 3, in which ΔT was calculated based on the difference of $T_d$ obtained from the control hair and the corresponding treated hair with the end products.

TABLE 2

| Test Group No. | Hair | Reactant Product | Characteristic Life Time | Normalized Data | DSC ΔT (° C.) |
|---|---|---|---|---|---|
| I | Caucasian virgin hair | None | 3479 | — | — |
| | 2x Bleached hair | None | 981 | — | — |
| | | Example 1 | 5781 | 589 | — |
| | | Example 3 | 8925 | 910 | 3.4 |

TABLE 3

| Test Group No. | Hair | Reactant Product | Characteristic Life Time | Normalized Data | DSC ΔT (° C.) |
|---|---|---|---|---|---|
| II | Caucasian virgin hair | None | 6838 | — | — |
| | 2x Bleached hair | None | 1241 | — | — |
| | | Example 5 | 9723 | 783 | 1.9 |
| III | 2x Bleached hair | None | 2940 | — | — |
| | | Example 2 | 6184 | 210 | 11.7 |
| | | Example 7 | 7838 | 267 | 11.7 |
| IV | 2x Bleached hair | None | 5843 | — | — |
| | | Example 4 | 12306 | 211 | 10.9 |
| V | 2x Bleached hair | None | 6103 | — | — |
| | | Example 8 | 5978 | 98 | 11.2 |

The results show that, after the treatment of double-bleached hair with the samples obtained from the presently disclosed and/or claimed inventive concept(s), the anti-stressing capacity of the damaged hair is strengthened in comparison with the untreated hair. Moreover, the strengths of the damaged hair are increased and even higher than those of virgin hair. The results also show that the denaturation temperature is higher for the treated hair compared to those untreated damaged hair.

Hair Color Protection

Virgin dark Caucasian hair was dyed with Clairol Textures & Tones 4R (Red Hot Red) at 40° C. for 45 minutes. The hair was then rinsed for 2 minutes. After rinsing, the hair was treated in 0.5 wt % of solution containing the sample of Example 5, or treated in rinse-off conditioner, or combination of the solution and the rinse-off conditioner for 1 minute. The hair was dried overnight. Then the hair was soaked either in water or a 2% shampoo solution for 45 minutes. Absorbance was measured at 490 nm on Cintra 20 double beam UV-vis spectrometer using the soaking solution. 2.5 ml cell with 12.5×12.5×45 mm was used for the measurement. The lower the absorbance the less color leached from the hair. Table 4 lists the measurement results.

TABLE 4

| Treatment | Soaking Solution | Absorb. |
|---|---|---|
| None | 2% Shampoo | 0.4507 |
| 0.5% Solution* | 2% Shampoo | 0.3053 |

TABLE 4-continued

| Treatment | Soaking Solution | Absorb. |
|---|---|---|
| None | Water | 0.444 |
| 0.5% Solution | Water | 0.3213 |
| Rinse-off Conditioner | 2% Shampoo | 0.1956 |
| Rinse-off Conditioner + 0.5% Solution | 2% Shampoo | 0.1603 |
| Rinse-off Conditioner | Water | 0.203 |
| Rinse-off Conditioner + 0.5% Solution | Water | 0.168 |

*containing 0.5 wt % of the sample of Example 5

What is claimed is:

1. A method of strengthening hair fibers comprising applying a hair composition represented by one or both of the following formulas:

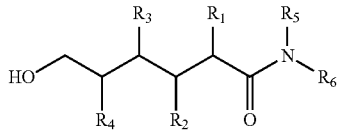

Formula (I)

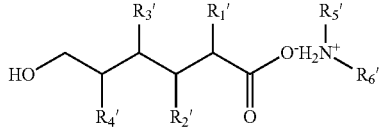

Formula (II)

wherein $R_1$-$R_4$ are a hydroxyl group, and $R_5$ and $R_6$ are independently hydrogen, or a —$CH_2CH_2CH_2OH$ group; and wherein $R'_1$-$R'_4$ are a hydroxyl group and $R'_5$ and $R'_6$ are independently hydrogen, or a —$CH_2CH_2CH_2OH$— group.

2. The method of claim 1, wherein a pH value of the hair composition is adjusted to about 2 to about 6 by using a buffer system.

3. The method of claim 2, wherein the buffer system comprises an acid or a salt.

4. The method of claim 3, wherein the acid is an organic acid selected from the group consisting of lactic acid, citric acid, tartaric acid, gluconolactive acid, pimelic acid, glyoxylic acid, aconitic acid, ethylenediaminetetraacetic acid, L-glutamic acid, malic acid, malonic acid, and combinations thereof.

5. The method of claim 3, wherein the acid is an inorganic acid selected from the group consisting of hydrogen chloride (HCl), sulfuric acid ($H_2SO_4$), nitric acid ($HNO_3$), phosphoric acid ($H_3PO_4$), and combinations thereof.

6. The method of claim 1, wherein the hair composition further comprises at least one active hair benefit component selected from the group consisting of surfactants, fatty acid soap, hair and skin conditioning agents, suspending aids, emollients, emulsifiers, rheology modifiers, thickening agents, vitamins, hair growth promoters, self-tanning agents, sunscreens, skin lighteners, anti-aging compounds, anti-wrinkle compounds, hair coloring treatment agents, hair color protecting agents, hair styling products, anti-cellulite compounds, anti-acne compounds, anti-dandruff agents, anti-inflammatory compounds, analgesics, antiperspirant agents, deodorant agents, hair fixatives, particulates, abrasives, moisturizers, antioxidants, keratolytic agents, anti-static agents, foam boosters, hydrotropes, solublizing agents, chelating agents, antimicrobial agents, antifungal agents, pH adjusting agents, chelating agents, buffering agents, botanicals, hair colorants, oxidizing agents, reducing agents, hair and skin bleaching agents, pigments, anticaries, antitartar agents, anti-plaque agents, solvents, and combinations thereof.

7. The method of claim 6, wherein the rheology modifier is a polymer selected from the group consisting of carboxymethyl cellulose, hydroxyethyl cellulose, hydroxypropyl cellulose, hydroxypropylmethyl cellulose, hydroxypropyl guar, hydroxymethyl hydroxyethyl cellulose, and combinations thereof.

8. The method of claim 7, wherein the rheology modifier is present in an amount ranging from about 0.1 to about 1.5 wt % based on the total weight of the hair composition.

9. The method of claim 1, wherein the hair fibers comprise virgin hair fibers, damaged hair fibers, bleached hair fibers, or colored hair fibers.

* * * * *